United States Patent [19]
Fry et al.

[11] Patent Number: 5,036,855
[45] Date of Patent: * Aug. 6, 1991

[54] LOCALIZATION AND THERAPY SYSTEM FOR TREATMENT OF SPATIALLY ORIENTED FOCAL DISEASE

[75] Inventors: Francis J. Fry; Narendra T. Sanghvi, both of Indianapolis, Ind.

[73] Assignee: Laboratory Equipment, Corp., Mooresville, Ind.

[*] Notice: The portion of the term of this patent subsequent to Aug. 22, 2006 has been disclaimed.

[21] Appl. No.: 370,269

[22] Filed: Jun. 22, 1989

Related U.S. Application Data

[63] Continuation of Ser. No. 163,259, Mar. 2, 1988, Pat. No. 4,858,613.

[51] Int. Cl.⁵ .................... A61B 17/22; A61B 8/00
[52] U.S. Cl. ..................... 128/660.03; 128/24 A; 128/662.06
[58] Field of Search ............. 128/660.03, 660.09, 128/660.1, 24 A; 606/128

[56] References Cited

U.S. PATENT DOCUMENTS

| | | | |
|---|---|---|---|
| 4,455,872 | 6/1984 | Kossoff et al. | 128/660.09 X |
| 4,485,819 | 12/1984 | Igl | 128/660.09 |
| 4,669,483 | 6/1987 | Hepp et al. | 128/660.03 |
| 4,821,730 | 4/1989 | Wurster et al. | 128/660.03 |
| 4,844,079 | 7/1989 | Naser et al. | 128/660.03 |
| 4,858,613 | 8/1989 | Fry et al. | 128/660.09 X |

*Primary Examiner*—Francis Jaworski
*Attorney, Agent, or Firm*—Woodard, Emhardt, Naughton, Moriarty & McNett

[57] ABSTRACT

A transducer assembly for visualization and treatment of transcutaneous and intraoperative sites includes in combination a visualization transducer and a treatment transducer, each of which are movable with both linear and rotary degrees of freedom. Movement of each transducer is by various motor and geared drive arrangements wherein certain degrees of freedom for one transducer are separate and independent from the degrees of freedom for the other transducer. At least one degree of freedom for each transducer is common and the transducers are moved concurrently.

One arrangement of the transducer combination is for prostate treatment and includes a specific shape and configuration for anatomical considerations and a control unit which is operable external to the patient to control both transducers and a reflective scanner which are inserted into the patient as part of the ultrasound probe.

2 Claims, 6 Drawing Sheets

LOCALIZATION AND THERAPY SYSTEM FOR TREATMENT OF SPATIALLY ORIENTED FOCAL DISEASE

This application is a continuation of application Ser. No. 163,259, filed 3/2/88, now U.S. Pat. No. 4,858,613.

BACKGROUND OF THE INVENTION

The present invention relates in general to the treatment of disease, tumors, etc., by the use of ultrasound. More particularly the present invention relates to a combined visualization and treatment device using ultrasound for both functions. Treatment is achieved by ablation of tissue representing the disease entity.

A large number of diseases manifest themselves in whole or in part in a focal manner. These include, for example, diseases of or in the brain, breast, liver and prostate. While surgical procedures have traditionally been employed when medicinal approaches were not suitable or effective, surgery still represents a significant risk to the patient and a chance that the entirety of the disease entity will not be completely removed.

There is no dispute as to the value of noninvasive treatment as such as producing volume lesions with focused ultrasound. One difficulty though with ultrasound treatment procedures is the need to visualize the disease entity and thereby determine the size, shape and location. While this concern does not normally exist with invasive techniques such as surgery, it is of critical concern in noninvasive procedures.

In our pending application entitled ULTRASOUND BRAIN LESIONING SYSTEM, filed on even date herewith, a visualization technique is described for volume lesioning treatment of a brain tumor. The technique involves a use of ultrasound or CT or MRI scan transparencies whose data is digitized into a computer and the landmark references from a skull fixation apparatus are used to preprogram the drive system for the transducer. By computer control, the brain tumors are located and the transducer automatically programmed for positioning such that the focused ultrasound beam is directed at each tumor and the dosage set to produce volume lesions.

An alternative to this position translation technique for brain tumors is to use ultrasound to visualize the disease entity. Since brain lesioning is somewhat unique due to the CT or MRI scans and the skull fixation apparatus, the visualization technique of our co-pending application may not be the most appropriate technique for ablation of other focal disease sites.

Since some of these other disease sites may be most effectively treated by the use of ultrasound in either a transcutaneous or intraoperative mode, there is a need to insure that the transducer components which are designed and the materials selected be such so as to be suitable for steam autoclaving.

The present invention provides an ultrasound localization and therapy system which is designed with both a visualization transducer and a therapy transducer. Those portions of the structure which must be sterilized are constructed from selected materials which are steam autoclavable.

Another concern with the treatment of disease in a transcutaneous mode by ultrasound is the physical size and shape of the probe. Since the transducer design of the co-pending application is used external to the patient, size and packaging considerations are not substantial. However, with the modes of examination and treatment such as transrectal, transesophogeal, etc., the probe design is critical. While the specifics of our co-pending transducer design may be used in some embodiments of the present invention, it will require some scaling down in size. Further, if the transducer assembly is going to be steam autoclavable, certain material changes are advisable in order to provide a finished product which will withstand the high autoclaving temperatures.

In a related embodiment the concept of utilizing a visualization transducer in combination with a treatment transducer is disclosed for treatment of the prostate. This particular configuration is adaptable for use in other body cavities. The therapy treatment from within such body cavities by ultrasound, where ultrasound is also used for imaging of the area to be treated, has not heretofore been done.

SUMMARY OF THE INVENTION

A visualization and treatment transducer for producing lesions in diseased tissue sites according to one embodiment of the present invention comprises a transducer housing having a main section and a detachable enclosure, movable visualization transducer means disposed within the detachable enclosure, movable treatment transducer means disposed within the detachable enclosure, first drive means providing rotary motion to the visualization transducer means in two degrees of freedom, second drive means providing rotary motion to the treatment transducer means in two degrees of freedom, the visualization transducer means and treatment transducer means having generally coaxial focal axes and the first and second drive means being operable independently of each other.

A transrectal or other body cavity visualization and treatment transducer assembly for ultrasonic visualization and treatment by producing lesions in diseased tissue sites according to another embodiment of the present invention comprises a fluid-filled, flexible-walled enclosure, a movable visualization transducer disposed within the enclosure, a movable treatment transducer disposed within the enclosure, a reflective scanner disposed within the enclosure and aligned with the treatment transducer for changing the direction of the focused ultrasound beam from the treatment transducer, first drive means providing rotary motion to the treatment transducer, second drive means providing linear motion to the visualization transducer, the first and second drive means being operable independently of each other, and third drive means providing rotary motion to the visualization transducer and the treatment transducer concurrently.

One object of the present invention is to provide an improved transducer assembly including both a visualization transducer and a cooperating treatment transducer.

Related objects and advantages of the present invention will be apparent from the following description.

DESCRIPTION OF THE PREFERRED EMBODIMENT

Figure 1:
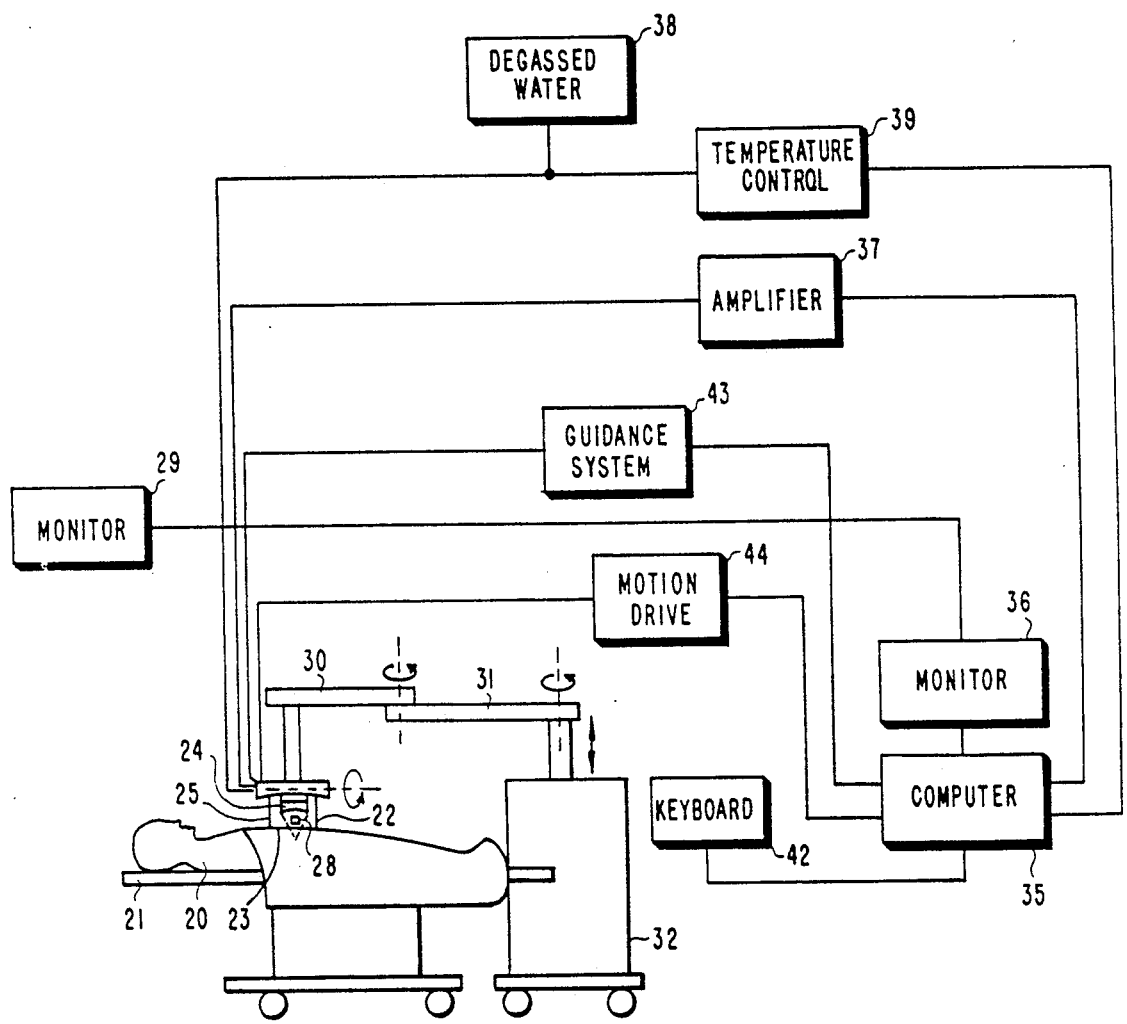
FIG. 1 is a diagrammatic illustration of an ultrasound treatment apparatus according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
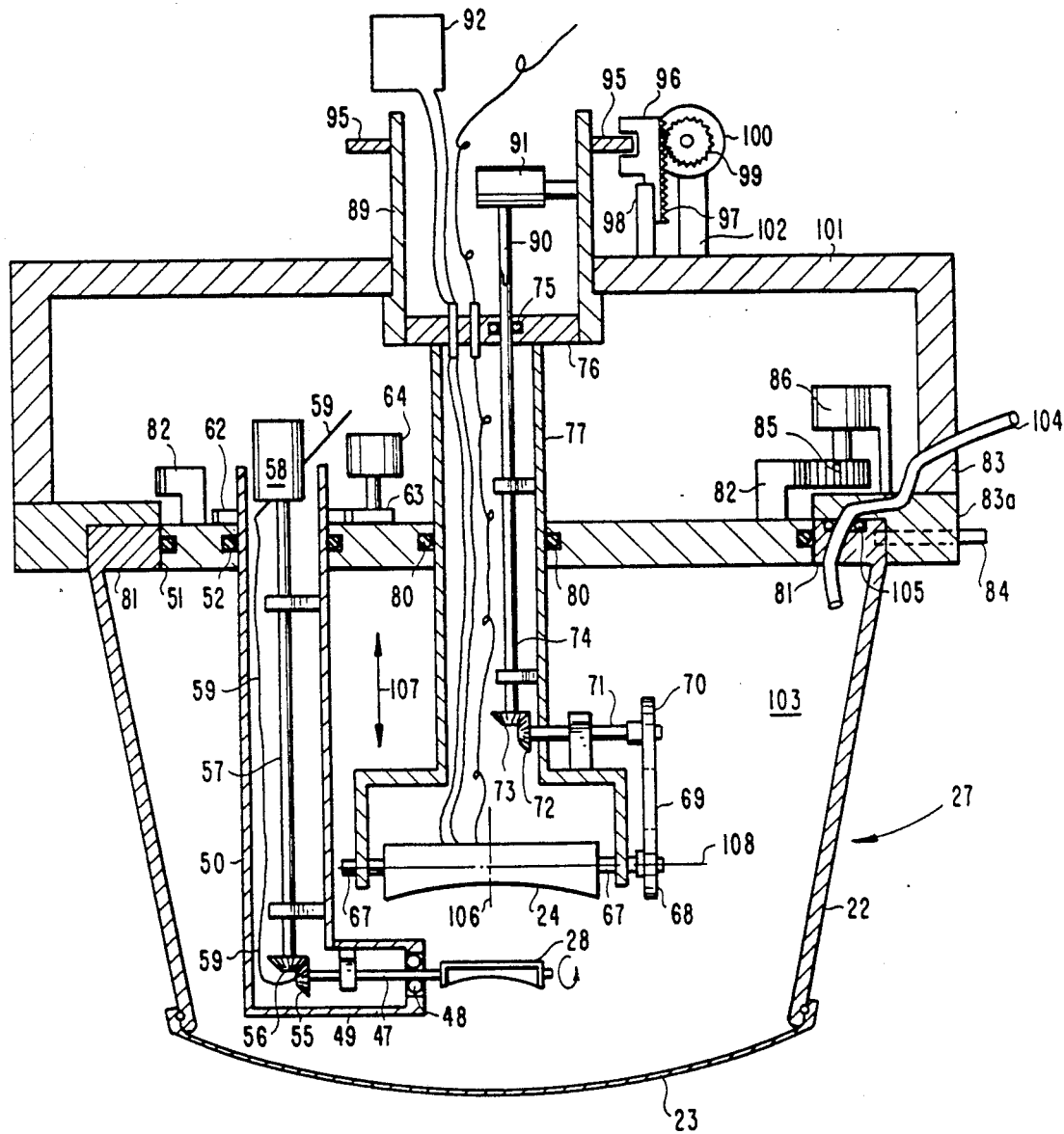
FIG. 2 is a side elevation, diagrammatic illustration of a transducer assembly which is suitable for use in the FIG. 1 apparatus.

Referring to FIG. 1, there is illustrated an ultrasound treatment system generally in block diagram form with the patient 20 lying on an appropriate table 21 with the transducer housing 22 diaphragm 23 in contact with the patient. A suitable coupling medium is used between the diaphragm and patient and the therapy transducer 24 is disposed in a volume of degassed water 25. In an intraoperative mode, sterile housing 22 with its diaphragm 23 is brought into contact with sterile fluid overlying on the internal organ or tissue directly. Guidance to the tissue or organ site is provided by ultrasound visualization element 28 located inside housing 22. The relative sizes and positional relationships of therapy transducer 24 and visualization element 28 which is an imaging transducer is best illustrated in FIG. 2.

Housing 22 is manually placed in position by the operator while being guided by transducer 28 with the ultrasound image displayed on monitor 29. Housing 22 is supported by articulating arms 30 and 31 with rotation axes as shown by the rotary arrows. Vertical motion is shown emanating from base support 32. Once the system is appropriately located for treatment, the articulating arms and rotation axes are locked in place. From the scanning of visualization transducer 28, the treatment volume is defined and stored in computer 35. The spatial position of the treatment volume is also defined with respect to depth and orientation to surrounding tissues. By interacting with the tissue and organs displayed on monitor 36, the treatment spatial regimen is computed. Dosage parameters of sound intensity and time-on period are entered into computer 35.

Once the treatment regimen is established, the system automatically progresses through the treatment volume by placing individual focal ablative lesions. Power amplifier 37 provides the drive energy to therapy transducer 24 for each focal site under control of computer 35. Degassed water system 38 provides degassed water to the interior of transducer housing 22 and temperature control system 39 keeps this degassed water at a constant temperature during the therapy procedure. The procedure can be interrupted at any time by the operator and restarted at the last stopped position, if that is desired.

In the event the operating and control electronics are remote from the patient, which would be the typical case, local keyboard control 42 is provided for at-site interfacing with the computer 35. Also interfacing with computer 35 are the ultrasound guidance and site placement system 43 and the motion drive and control apparatus 44.

Referring to FIG. 2, transducer assembly 27 is illustrated. Assembly 27 includes visualization transducer 28 which is a spherical ceramic piezoelectric element mounted in a metal ring. Hollow metal rod 47 attaches to this metal ring and runs through O-ring seal 48 in metal housing 49. Housing 49 is attached to metal housing 50 which runs through plate 51 and is sealed by O-ring 52. Transducer 28 is mechanically rotated (as shown by arrow) in a sector motion by rotation of rod 47 which is driven through bevel gears 55 and 56. Gear 55 is attached to rod (shaft) 47 and gear 56 is attached to drive shaft 57. Shaft 57 is driven in a rotary fashion by motor 58 which incorporates an encoder so that the angular position of transducer 28 is known. Knowing the angular position of transducer 28 provides angular information for the sector format (visualization) display. Electrical driving pulses and receiving pulses to transducer 28 go through wire lead 59 which attaches to the piezoelectric element in transducer 28 through the center hollow portion of rod 47. Transducer 28 is rotated in a plane normal to the plane of the paper from beneath transducer 22 by rotating tubular housing 50 using attached gear 62 which meshes with gear 63 driven by stepping motor 64 which has an encoder to establish the position of transducer 28 in this particular plane of rotary motion.

Transducer 24 is rotated on axis elements 67. This rotation is accomplished through sprocket gear 68 driven by belt 69 which in turn is driven by sprocket 70. Sprocket 70 is driven by shaft 71 which in turn is driven in a rotary manner by meshed bevel gears 72 and 73. Bevel gear 73 is attached to and driven by shaft 74. Shaft 74 is rotatable through O-ring seal 75 in top plate 76 which is attached to tubular housing 77. Transducers 28 and 24 are positioned so that their respective ultrasound beam focal axes are substantially coaxial to each other.

Tubular housing 77 is movable up and down relative to plate 51 through O-ring seal 80. Plate 51 is rotatable in ring 81 through ring gear 82 mounted to plate 51 and running entirely around the apparatus (360° circle). The parts including and below plate 51 and ring 81 are detachable from ring 83 for autoclaving. Ring 83a is illustrated as a separate piece but is in fact rigidly attached to ring 83. These components remain with the support (articulating) arms during the autoclaving procedure for the parts which are detached. Similarly, gear 85 is not removed for autoclaving. For autoclaving top plate 76 is removed with housing 77 and plate 51.

After autoclaving plate 51 and ring gear 82 are inserted in ring 83 and attached by a plurality of pins 84 positioned around the periphery of ring 83a. Rotation of plate 51 is accomplished through circular ring gear 82 driven by gear 85 attached to stepping motor 86 which includes an encoder. When plate 51 rotates all attached members including transducer 24 rotate concurrently. Plate 76 meshes with tube 89 on insertion of plate 51 and ring 81. When plate 76 meshes, drive shaft 74 meshes with shaft 90 which is attached to stepper motor 91 which includes an encoder.

Electrical drive power to transducer 24 is also coupled as is pressure system 92 when plate 51 and ring 81 are inserted. Vertical motion of transducer 24 is accomplished through ring 95 attached to tube 89 which links with plate 76. Ring 95 can rotate freely in element 96 which is driven up and down by gear rack 97 attached to element 96. Element 96 is constrained by slide system 98. Gear rack 97 is driven by gear 99 which is attached to stepper motor 100 and includes an encoder which is supported off the top surface 101 of ring 83 by member 102. Filling of chamber 103 with degassed water 25 is accomplished through tubing member 104 which is coupled through O-rings 105 to ring 81. Bath temperature in 103 is maintained by coils which circulate controlled-temperature fluid introduced through tubing 104.

Therapy transducer 24 is provided with three degrees of freedom. The unit can be rotated about axis 106, it can be moved up and down as shown by arrow 107, and it can be rotated about axis 108. Use of these motions permits volume lesions to be made after unit 27 is locked in position.

Figure 3:
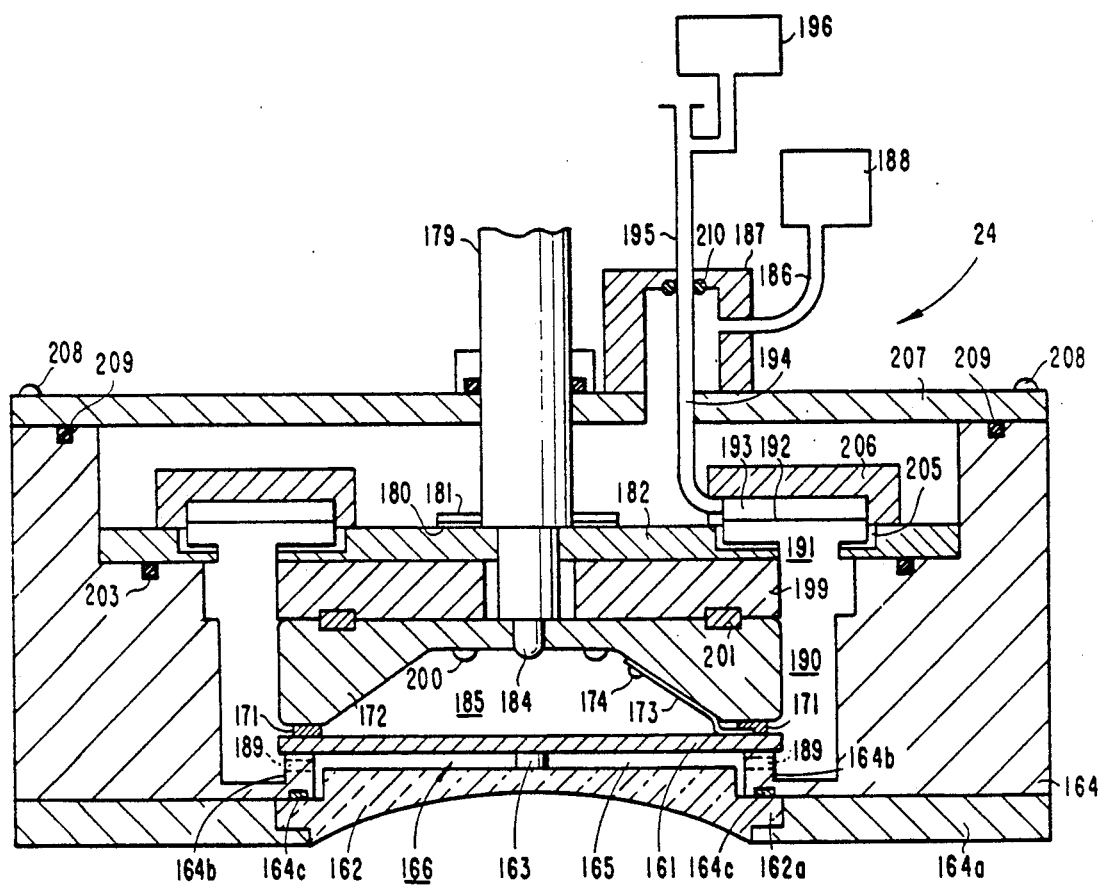
FIG. 3 is a front elevation, diagrammatic illustration in full section of a transducer design suitable for use in the FIG. 2 transducer assembly.

Referring to FIG. 3, internal details of therapy transducer 24 are illustrated in greater detail. It should be noted that this illustration does not include axis elements 67 and the power cable which is diagrammatically shown in FIG. 2 as a coiled wire connecting to the transducer is, in the FIG. 3 illustration a coaxial cable. While FIG. 2 discloses an air pressure system 92 for some of the interior spaces, FIG. 3 further includes a similar air pressure system 188 and an air pressure system 196 for controlling the silicone oil pressure for other interior spaces within transducer 24.

Referring to FIG. 3, transducer 24 is configured with several unique features which are provided in order for a stable acoustic output to be obtained at all preselected driving levels. These driving levels are required in order to produce controlled focal lesions. In order to achieve this necessary objective, it is necessary to have a stable sound-producing source such as generally circular (disc) quartz plate 161 which is used in this particular embodiment. The quartz plate 161 is able to be maintained flat and parallel to generally circular, planoconcave lens 162 by the structure which will be described hereinafter. Lens 162 is a hard anodized aluminum lens with an elliptic concave surface for minimizing the half-intensity length of the beam at the focus. In order to maintain flatness and parallelism of plate 161 and lens 162 with a fixed spacing distance therebetween, the aluminum flat side of the lens is precisely machine flat with at least one $\frac{1}{8}$ inch diameter rod 163 machined on the surface to extend a distance above the lens surface equal to a $\frac{1}{4}$ wave length in the silicone oil which is disposed in space 165.

In order to maintain this $\frac{1}{4}$ wave length spacing to within plus or minus 0.0001 inches, it is required that the outer peripheral lip 162a of aluminum lens 162 provide unanodized surfaces (flat top and bottom surfaces and outer edge surface) which rest directly in contact with the flat machined surface of housing 164 and end plate 164a. Housing 164 includes an inwardly and upwardly directed lip 164b, of an annular ring configuration, whose underside abuts against the top surface of lip 162a and whose top surface supports plate 161. The height of this lip is precisely machined since it is the means to fix the $\frac{1}{4}$ wave length separation between the plate 161 and lens 162. Rod 163 provides center stabilizing for the plate due to its span between peripheral edge supports and the pressure differential between the top and bottom surfaces of the quartz plate. The space 165 between the plate 161 and lens 162 (the $\frac{1}{4}$ wave length spacing) is filled with silicone oil 166 which is freely exchanged through radially open channels in lip 164b. A suitable silicone oil for this application is Dow Corning 710 fluid. Gasket 164c seals the oil in space 165.

One gold-plated and polished electrode, electrically connected to quartz plate 161, rests in direct contact with the top machined surface of lip 164b and provides the electrical ground contact for the quartz plate.

In order to keep plate 161 in pressure contact with housing 164, a flat, flexible gasket 171 is firmly pressed against plate 161 through metal member 172. In order to provide electrical contact for power to plate 161 an electrode 173 fabricated of an approximate 0.001 thick soft metal foil (gold, brass, silver) extends part-way under compression gasket 171, while the remainder of gasket 171 acts as a seal for the silicone oil. The power and ground electrodes on plate 161 do not extend to the edge of plate 161 and the silicone oil provides insulation around the edge. The foil electrode 173 is attached to metal member 172 with a series of metal screws 174.

To provide RF power to drive quartz plate 161 a coaxial cable 179, with metal sheath 180 drawn back and clamped under plate 181 to metal plate 182, is provided. The coaxial cable has an end plug 184 which side pressure contacts plate (metal member) 172 through a central hole. Space 185 is an air space so that the quartz plate 161 is not back acoustically loaded thereby directing all its acoustic output through the interspace 165 and lens 162 into the fluid which is in front of lens 162. To insure flatness of quartz plate 161 and parallelism with the flat surface of lens 162, the air space 185 and all other air spaces in the transducer housing 164 are pressurized through tube 186 into element 187. This air pressure holds quartz plate 161 against machined rod 163 to maintain the necessary parallelism. Pressure is applied from source 188.

In order to maintain a positive differential pressure in space 185 relative to the pressure in interspace 165, flow communication is provided from interspace 165 via flow access channels 189 into column 190 and well 191. These areas are all silicone oil filled and in pressure equilibrium is a thin flexible diaphragm 192 which covers well 191. Above diaphragm 192, the air space 193 is exhausted through flexible tubing 194 and rigid tube 195 to the outside atmosphere.

A further feature to suppress cavitation in the oil in space 165 between the quartz plate 161 and lens 162 when the system is run at the highest acoustic output power is provided by pressure system 196 providing greater-than-atmospheric pressure to space 193. Typically this pressure will be that which prevents any cavitation in space 165 (of the order of 40-50 pounds per square inch). This pressure in space 193 is readily transmitted through diaphragm 192 to the silicone oil in well 191 and hence through column 190 into space 165. The pressure provided by source 188 is in the order of 2 pounds per square inch higher than the pressure in system 196 in order to keep plate 161 flat and held against lens 162 through rod 163.

Element 199 in the transducer assembly is an insulating member to which element 172 is bolted by screw(s) 200. Gasket 201 keeps the silicone oil contained in column 190 from reaching the coaxial cable 179. Metal plate 182 is bolted to housing 164 around the outer periphery of plate 182. Oil is kept in column 190 and well 191 by the use of O-ring seal 203 positioned between housing 164 and plate 182 and by gasket 205. Member 206 is bolted and sealed to plate 182. Top metal plate 207 is bolted by screws 203 to housing 164 and sealed thereto through O-rings 209. Metal tube 195 is sealed to element 187 through seal 210. The coaxial cable 179 is water-tight and sealed to top plate 207 through member 211 and O-ring 212.

In order to accomplish the task of producing lesions of any complex size or shape with intense focused ultrasound it is necessary to provide for ultrasound dosage conditions which produce individual focal lesions (from which the complex volume can be generated), which do not compromise tissue outside the intended focal lesions side and permit subsequent individual focal lesions in a contiguous manner. When transducer 24 is used for the treatment of brain tumors by creating lesions in deep brain sites in both gray and white matter and abnormal brain tissue, it is necessary to inhibit the production of microbubble formation at the primary focal site so that there can be no vascular dispersion of such microbubbles away from the primary focal site which microbubbles could initiate off primary site lesion production and hemorrage due to ultrasound passage through microbubble comprised tissue.

In order to accomplish this task while being able to accomplish primary site lesions, it is necessary to derive these sound intensities as a function of frequency which will not produce microbubbles at the primary lesion site. This requires that for a 1 MHz sound frequency (a frequency necessary to achieve deep penetration into the human brain), the primary site sound intensity must not exceed 300 watts per square centimeter. At this intensity and for lower intensities, gray and white matter lesions on a multiplicity of individual contiguous sites can be produced without undesirable side effects (microbubbles). As the frequency is increased above 1 MHz, the primary site sound intensity can be increased and produce no microbubbles but the penetration capability in brain tissue returns as the sound frequency is increased. At 4 MHz frequency which is the upper frequency which can be considered for more superficial brain lesion production, the intensity which will not lead to microbubble formation is at least 2100 watts per square centimeter. At these intensity limits, the time-on period of sound irradiation at each individual site can be extended to as many seconds as is needed to ablate the tissue at the focal site without microbubble formation.

In order to constrict the individual lesion sites so that the boundaries of desired volume lesions can be constrained, the transducer configuration used will give a half intensity length at the lesion focal region in the order of 15 mm at 1 MHz operating frequency. This length of half intensity is consistent with the necessity of constraining lesions in the human brain so that the extending of individual lesions into white matter (white matter is more sensitive than gray matter) can also be constrained.

Still referring to FIG. 3, in order to make the transducer assembly 27 capable of being steam autoclaved, gasket 171 needs to be made from fluorosilicone in order to take the high autoclave temperature and resist the uptake of the silicone oil which is used within the assembly. A suitable silicone oil for this application is Dow Corning 710 fluid which has the necessary high temperature resistance. All gaskets in contact with the Dow Corning 710 fluid must be made of fluorosilicone. All other O-rings and gaskets not in contact with the Dow Corning 710 fluid can be made of silicone. Insulator 199 must be a high-temperature plastic, such as, for example, General Electric's Ultem. Coaxial cable 179 must also include high-temperature materials such as Teflon insulation. The volume expansion chamber (well) 191 requires a fluorosilicone membrane 192 which must be capable of taking the volumetric expansion of the silicone oil during the autoclaving procedure. The system design requires that all differential expansions be accounted for when the steam autoclaving is performed.

As previously pointed out, one of the primary concerns with transcutaneous and intraoperative modes of ultrasound treatment is the need to design the transducer assembly so that those portions that need to be autoclaved can be steam autoclaved. Recognizing that the entirety of the assembly will not be contaminated by use in the prior treatment procedure, only selected components need to be autoclaved and these are detachable as previously described. Another concern is the ability to visualize the area for treatment. In order to guide and manuever the therapy (treatment) transducer to the appropriate ablation sites within the body, some visualization means must be employed. In the disclosed embodiment of FIGS. 1-3, the visualization means is the visualization transducer 28. Yet another concern with a transcutaneous mode of treatment is the size and shape of the probe (transducer assembly and housing). Transcutaneous modes may include transrectal or transesophogeal, for example.

Localization and treatment (tissue destruction) of the prostate by way of a transrectal route requires both the ability to localize the treatment volume and then to apply the treatment regimen in that identified volume. One configuration to accomplish this particular task is described in FIGS. 4-8.

Figure 4:
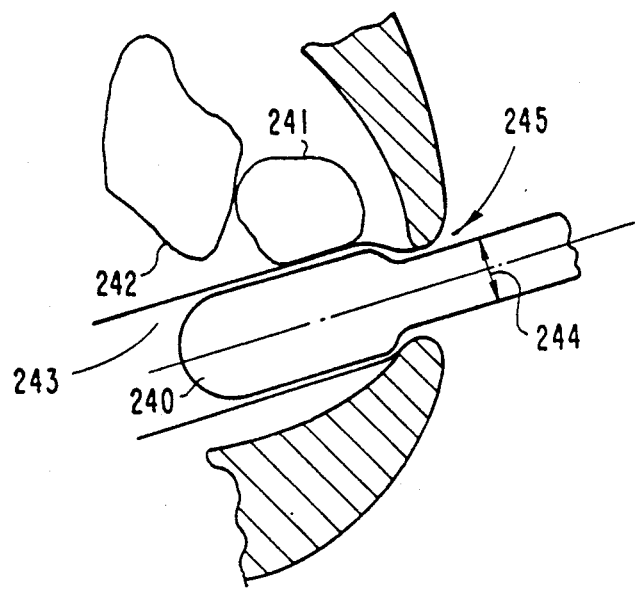
FIG. 4 is a perspective, diagrammatic illustration of an ultrasonic probe for prostate visualization and treatment.

In the FIG. 4 embodiment, ultrasound probe 240 is illustrated as inserted into the rectum and positioned for visualization and treatment of the prostate 241. Also illustrated and positioned in FIG. 4 are the urinary bladder 242 and rectum 243. Diagrammatically illustrated is a cross-section area of the tapered stem of probe 240 in order to show the entry diameter 244. The probe is inserted by way of the rectal entry region 245.

Figure 5:
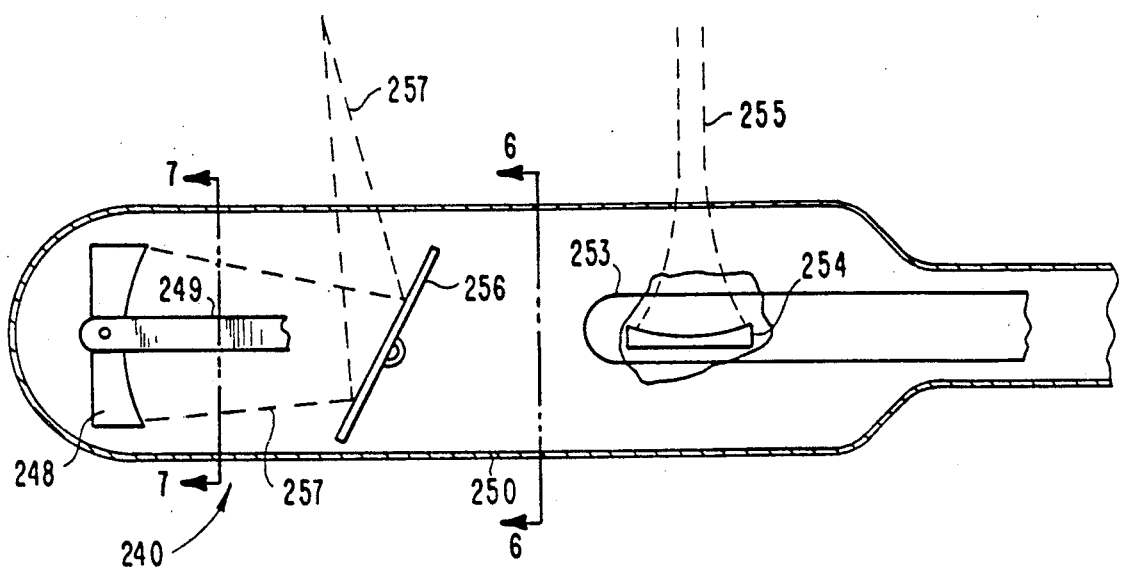
FIG. 5 is a side elevation, diagrammatic illustration of the FIG. 4 ultrasonic probe.

Referring to FIG. 5, the internal features and components of probe 240 are diagrammatically illustrated. In answer to concerns previously mentioned, probe 240 includes a focused transducer 248 for delivering the therapy (abalation) which is supported by and movable relative to arm elements 249 positioned within flexible envelope 250. Envelope 250 is filled with water so as to expand to contact the rectal wall, but by removal of some water and some rotation of transducer 248 and mirror 256, the size is reduced to make entry easier. Arm elements are curved so that when the unit is in the rectum, the diameter at the entry of the probe is smaller than the remainder.

Visualization element 253 includes in its interior space transducer 254 which is operable to generate ultrasound imaging beam 255 in the direction of the prostate. Transducer 248 is movable in a rotary manner relative to elements 249 and has a focused beam directed at circular (disc) mirror 256 which is adapted to bend and redirect beam 257 toward the desired region of the prostate. The movement of transducer 248 relative to mirror 256 is used to affect the depth of the beam (focused spot) into the prostate. Since the transducer beam has a fixed focus, the less of the beam length used between the transducer and mirror, the longer the beam length reflected from the mirror. Transducer 248 is also movable linearly with mirror 256 along the longitudinal axis of probe 240. The entire probe portion is rotatable by external means as illustrated in FIG. 8.

Figure 6:
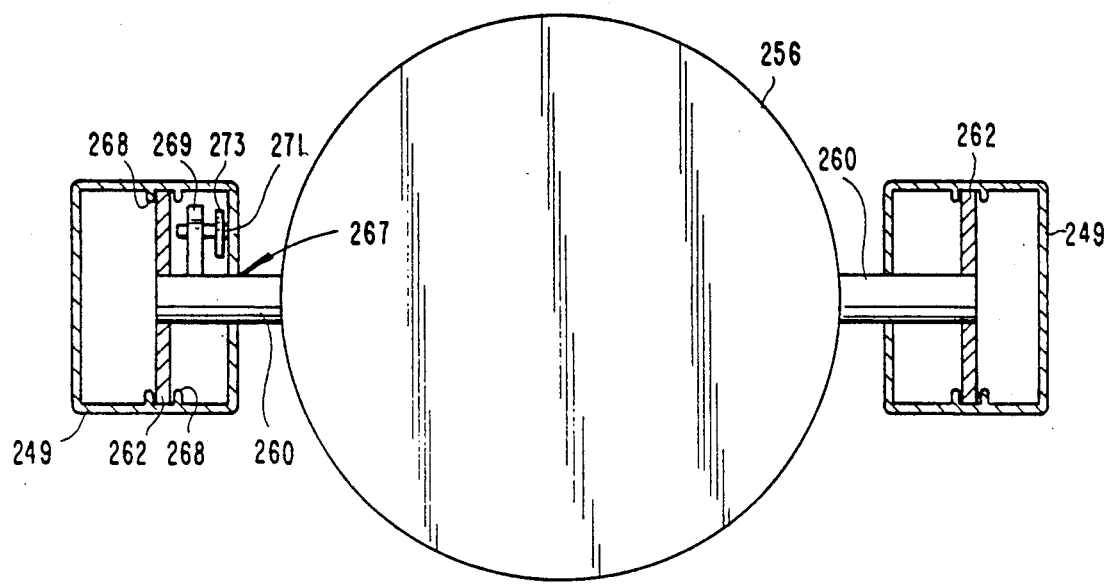
FIG. 6 is a lateral section view of the FIG. 4 ultrasonic probe detailing the configuration and support of a reflective scanner.
Figure 7:
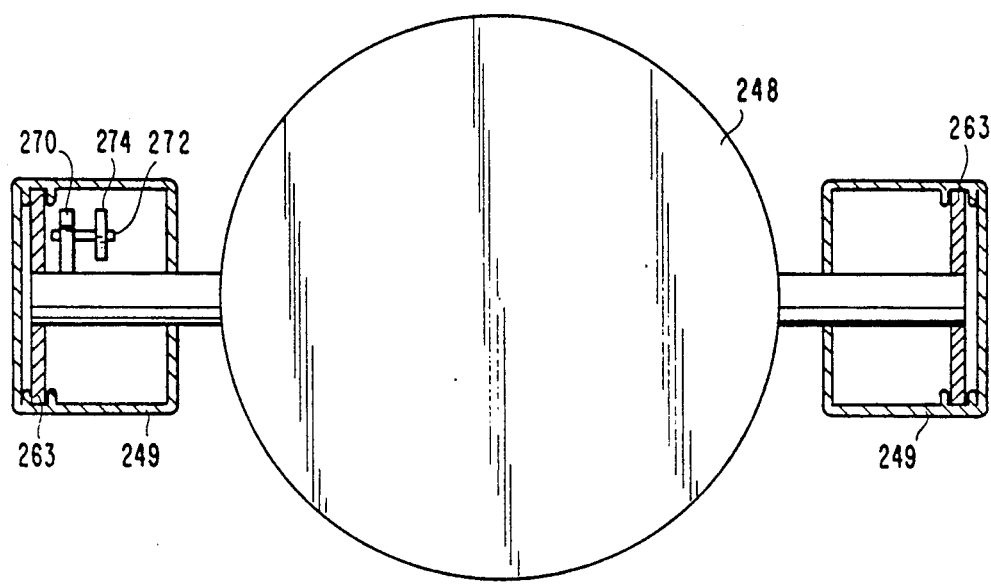
FIG. 7 is a lateral section view of the ultrasonic probe detailing the arrangement and support of the treatment transducer.

Referring to FIG. 6, the support of mirror 256 by arm elements 249 and related components is illustrated in greater detail. As previously described, elements 249 which support transducer 248 and by means of rotary and sliding extensions 260 also support mirror 256. Arm elements 249 are thin-walled, hollow, flexible tubes open at their proximal end for the exiting of elements 262 and 263 (FIG. 7) and bands 273 and 274 (FIG. 7). Extensions 260 rigidly attach to mirror 256 and extend through slot 267 so that linear movement of the mirror relative to elements 249 can be affected. Extensions 260 fit within elements 262 for rotary motion and elements 262 travel in top and bottom tracks 268 formed as part of the interior wall surface of element 249. Referring to FIG. 7, the extension of elements 249 and their coupling to transducer 248 is illustrated. Both FIGS. 6 and 7 should be regarded as lateral sections looking along the longitudinal axis of the ultrasonic probe 240 with the mirror and transducer oriented so as to reveal their full disc (circular) configuration. The structure of FIG. 7 is virtually the same as FIG. 6 with one main difference. The rotational and linear travel linkage made up of elements 263, 270, 272 and 274 for transducer 248 is outward, relative to element 249, from elements 262, 269, 271 and 273 for the mirror. This allows the linear travel of the mirror to be separately controlled as well as the rotation relative to element 263, without interference between the transducer and mirror and their linkages.

Figure 8:
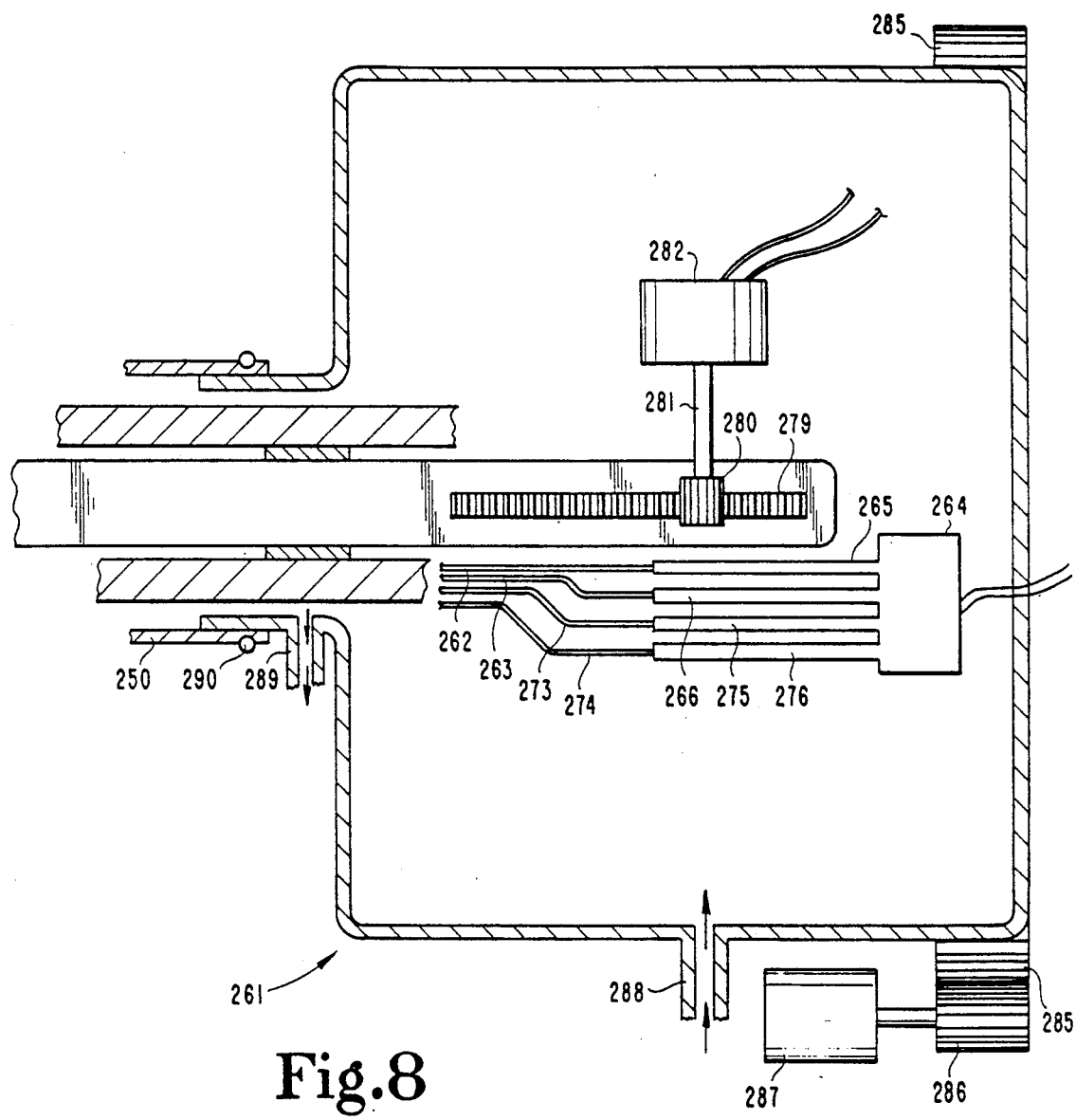
FIG. 8 is a side elevation, diagrammatic illustration in full section of a control unit which is coupled to the FIG. 4 probe for imaging and treatment control.

Referring now additionally to FIG. 8, control unit 261 which attaches to the reduced diameter end of probe 240 is illustrated. The linear movements on both transducer 248 and mirror 256 are accomplished by the linear translation of elements 262 and 263 which are flexible strips or bands so that they are able to accommodate the configurational bend in arm elements 249. Elements 262 and 263 are coupled to linear actuators and encoders, all of which are represented by block 264 through couplers 265 and 266. This arrangement permits coordinate linear translation of the therapy transducer and reflective mirror with respect to the visualization element 253 and the beam 255 generated by transducer 254. Rotation of focused transducer 248 and reflective mirror 256 is accomplished by crank arms 269 and 270. The crank arms with pins 271 and 272 are in turn driven by bands 273 and 274. These bands are connected to the linear actuators and encoders represented by block 264 by way of couplers 275 and 276. This particular arrangement permits the coordination of linear translation and/or relative translations to rotate the focused transducer 248 and reflective mirror 256.

On insertion of ultrasonic probe 240 into the rectal area, the focused transducer and reflective mirror are rotated so as to reduce as much as possible the overall outside contour of the probe upon entry into the patient. The mirror may be rotated on axis, i.e., relative to elements 249 in order to gain additional space within the probe for movement of the visualization transducer 254. Except for these two instances of mirror rotation, it remains rotationally fixed.

When visualizing the prostate elements, the focused transducer and reflective mirror are translated as shown so that free visualization of the prostate can be accomplished and then the transducer 248 and reflective mirror 256 positioned in order to place beam 257 at the positions delineated by beam 255. These position determinations are made through encoder determinations arrived at by computer computations. Visualization element 253 is linearly translated and encoded by rack 279, pinion 280, shaft 281, and drive motor with encoder 282.

In order to provide rotary motion in the rectum, the entire system including control unit 261 can be rotated through ring gear 285 driven by pinion or drive gear 286 and motor encoder 287.

Filling (and emptying) of the unit with degassed water is done through tubes 288 and 289 so that the entire system is water-filled and means for removing trapped air bubbles provided. This arrangement avoids sliding seals at the juncture between the insertable elements and the exterior elements. Flexible envelope 250 is attached to control unit 261 by slipping band 290 over the outer surface of envelope 250.

All electrical leads, some of which are shown diagrammatically, pass through water-tight seals in control unit 261. Electrical power to the focused transducer 248 is provided by an electrical lead which travels along arm element 249.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A visualization and treatment transducer assembly comprising:
   a transducer housing having a main section and a detachable enclosure;
   movable visualization transducer means disposed within said enclosure;
   movable treatment transducer means disposed within said enclosure;
   first drive means providing rotary motion to said visualization transducer means in two degrees of freedom;
   second drive means providing rotary motion to said treatment transducer means in two degrees of freedom;
   said visualization transducer means and said treatment transducer means having generally coaxial focal axes; and
   said first and second drive means being operable independently of each other.

2. A prostate visualization and treatment transducer assembly comprising:
   a fluid-filled, flexible-walled enclosure;
   movable visualization transducer means disposed within said enclosure;
   movable treatment transducer means disposed within said enclosure;
   reflective scanning means disposed within said enclosure and aligned with said treatment transducer means for changing the direction of the focused ultrasound beam from said treatment transducer means;

first drive means providing rotary motion to said treatment transducer means;

second drive means providing linear motion to said visualization transducer means;

said first and second drive means being operable independently of each other; and third drive means providing rotary motion to said visualization transducer means and to said treatment transducer means concurrently.

* * * * *